US011948307B2

(12) United States Patent
Watanabe et al.

(10) Patent No.: US 11,948,307 B2
(45) Date of Patent: Apr. 2, 2024

(54) SOLID-LIQUID BOUNDARY DETECTION DEVICE AND PRE-PROCESSING DEVICE PROVIDED WITH SAME (71) Applicants: NATIONAL UNIVERSITY CORPORATION KOBE UNIVERSITY, Kobe (JP); SHIMADZU CORPORATION, Kyoto (JP)

(72) Inventors: Tsutomu Watanabe, Kyoto (JP); Naoki Takamura, Kyoto (JP); Tomohisa Hasunuma, Kobe (JP)

(73) Assignees: NATIONAL UNIVERSITY CORPORATION KOBE UNIVERSITY, Kobe (JP); SHIMADZU CORPORATION, Kyoto (JP)

( * ) Notice: Subject to any disclaimer, the term of this patent is extended or adjusted under 35 U.S.C. 154(b) by 520 days.

(21) Appl. No.: 17/259,623

(22) PCT Filed: Jul. 10, 2019

(86) PCT No.: PCT/JP2019/027327
§ 371 (c)(1),
(2) Date: Jan. 12, 2021

(87) PCT Pub. No.: WO2020/017411
PCT Pub. Date: Jan. 23, 2020

(65) Prior Publication Data
US 2021/0295526 A1 Sep. 23, 2021

(30) Foreign Application Priority Data
Jul. 17, 2018 (JP) .................................. 2018-134179

(51) Int. Cl.
*G06T 7/13* (2017.01)
*C12M 1/00* (2006.01)
(Continued)

(52) U.S. Cl.
CPC ............... *G06T 7/13* (2017.01); *C12M 41/44* (2013.01); *C12M 45/05* (2013.01); *C12M 47/02* (2013.01);
(Continued)

(58) Field of Classification Search
CPC ... G06T 7/13; G06T 7/74; G06T 2207/30024; G06T 2207/10152; C12M 41/44;
(Continued)

(56) References Cited

U.S. PATENT DOCUMENTS 5,275,951 A * 1/1994 Chow ................ G01N 35/0098
422/930
6,456,944 B1 * 9/2002 Burkhardt .......... G01N 35/1016
73/864.22
(Continued)

FOREIGN PATENT DOCUMENTS

| JP | 2004-037320 A | 2/2004 |
| JP | 2012-080836 A | 4/2012 |
| JP | 2012-200239 A | 10/2012 |

OTHER PUBLICATIONS

Communication dated Dec. 14, 2021 from the Japanese Patent Office in Application No. 2020-531266.
(Continued)

*Primary Examiner* — William H. Beisner
*Assistant Examiner* — Danielle B Henkel
(74) *Attorney, Agent, or Firm* — Sughrue Mion, PLLC (57) ABSTRACT A solid-liquid boundary detection device 20 is a device for detecting a boundary 141 between a solid and a liquid in a test tube 14, and includes a surface illumination 21, an
(Continued)

imaging unit 22, and a boundary detection processor 31. The surface illumination 21 illuminates the test tube 14 from outside. The imaging unit 22 is arranged on an opposite side of the test tube 14 from the surface illumination 21, and captures an image including the boundary 141. The boundary detection processor 31 detects the boundary 141 from the image captured by the imaging unit 22.

3 Claims, 5 Drawing Sheets

(51) Int. Cl.
  *C12M 1/34*      (2006.01)
  *G06T 7/73*      (2017.01)
  *H04N 23/56*     (2023.01)
(52) U.S. Cl.
  CPC ............... *C12M 47/12* (2013.01); *G06T 7/74* (2017.01); *H04N 23/56* (2023.01); *G06T 2207/30024* (2013.01)
(58) Field of Classification Search
  CPC ...... C12M 45/05; C12M 47/02; C12M 47/12; C12M 29/00; C12M 33/10; H04N 23/56; G01F 23/292
  See application file for complete search history.

(56) References Cited

U.S. PATENT DOCUMENTS

| | | | |
|---|---|---|---|
| 2005/0156607 A1* | 7/2005 | Okamura | G01F 23/284 324/639 |
| 2007/0177778 A1* | 8/2007 | Massaro | G01N 35/1016 382/128 |
| 2012/0252110 A1 | 10/2012 | Oura et al. | |
| 2013/0230914 A1 | 9/2013 | Totani et al. | |
| 2018/0127695 A1 | 5/2018 | Nam et al. | |

OTHER PUBLICATIONS

Kyowa Interface Science Co., Ltd., "Contact angle meter Drop Master series", [Retrieved on Sep. 25, 2019], Mar. 14, 2013, pp. 1-4, Retrieved from the Internet, URL<https://ipros.ip/product/detail/2491004>, Ipros Manufacturing [online].

International Search Report of PCT/JP2019/027327 dated Oct. 8, 2019 [PCT/ISA/210].

Written Opinion of PCT/JP2019/027327 dated Oct. 8, 2019 [PCT/ISA/237].

* cited by examiner

SOLID-LIQUID BOUNDARY DETECTION DEVICE AND PRE-PROCESSING DEVICE PROVIDED WITH SAME

CROSS REFERENCE TO RELATED APPLICATIONS

This application is a National Stage of International Application No. PCT/JP2019/027327 filed Jul. 10, 2019, claiming priority based on Japanese Patent Application No. 2018-134179 filed Jul. 17, 2018.

TECHNICAL FIELD

The present invention relates to a solid-liquid boundary detection device for detecting a boundary between a solid and a liquid in a container, and a pre-processing apparatus provided with the same.

BACKGROUND ART

A technology has been known in which an analysis such as metabolome analysis is performed by culturing cells of microorganisms and plants in a culture medium in a culture vessel, collecting cells from the culture medium, performing pre-processing, and then supplying the cells to a liquid chromatograph mass spectrometer. In this kind of technology, a sampling apparatus for sampling a culture medium containing cells and a pre-processing apparatus for performing pre-processing on the cells contained in the sampled culture medium are used. The sampling of the culture medium is performed under an aseptic condition (refer to, for example, Patent Document 1 below).

In the pre-processing apparatus, for example, centrifugation is performed on the container in which the culture medium containing the cells is housed, by a centrifugation mechanism. As a result, the cells are accumulated as a solid at the bottom portion of the container or the like, and the cells (solid) and the liquid are separated from each other. In this state, when a needle is inserted into the container and the liquid in the container is sucked and removed from the tip end of the needle, only the cells (solid) can be collected.

PRIOR ART DOCUMENT

PATENT DOCUMENT

Patent Document 1: Japanese Patent Laid-Open No. 2012-200239

SUMMARY OF THE INVENTION

PROBLEMS TO BE SOLVED BY THE INVENTION

In a case where the solid and the liquid are separated as described above and only the liquid is sucked and removed, it is necessary to bring the tip end of the needle close to the boundary between the solid and the liquid. Almost all liquids can be sucked and removed if the tip end of the needle is brought as close to the boundary as possible in a range not coming into contact with the solid. Therefore, it is conceivable to detect the boundary between the solid and the liquid by using a photoelectric sensor or an ultrasonic sensor.

In the method using the photoelectric sensor, it is possible to detect the boundary between the solid and the liquid by detecting a change in color along a side surface of the container. However, depending on the way the light hits the container, the detection sensitivity may vary, and an error may occur in the position of the detected boundary.

In the method using the ultrasonic sensor, it is possible to apply ultrasonic waves from an upper portion of the container and detect the distance to the solid in the container. However, an error is likely to occur in the detection result of the boundary between the solid and the liquid, and the solid (cell) may be erroneously sucked by the needle.

The above-described problems may occur not only in a case where the cells as the solid are separated from the liquid and recovered, but also in a case where the solid other than the cells are separated from the liquid and recovered.

The invention has been made in view of the above circumstances, and an object of the invention is to provide a solid-liquid boundary detection device capable of accurately detecting the boundary between the solid and the liquid, and a pre-processing apparatus provided with the same.

MEANS FOR SOLVING THE PROBLEMS (1) A solid-liquid boundary detection device according to the invention is a device for detecting a boundary between a solid and a liquid in a container, and includes a surface illumination, an imaging unit, and a boundary detection processor. The surface illumination illuminates the container from outside. The imaging unit is arranged on an opposite side of the container from the surface illumination, and captures an image including the boundary. The boundary detection processor detects the boundary from the image captured by the imaging unit.

According to such a configuration, the container is uniformly illuminated from the outside by the surface illumination, and the image of the boundary between the solid and the liquid in the illuminated container can be captured by the imaging unit. Therefore, since the position of the boundary that becomes a shadow due to illumination does not shift due to the way the light hits, and the image is always captured at an accurate position, the boundary between the solid and the liquid can be detected more accurately.

(2) The solid-liquid boundary detection device may further include a pedestal portion and a movement mechanism. The pedestal portion receives a bottom portion of the container. The movement mechanism moves the pedestal portion in a direction intersecting a horizontal direction to position the container at an imaging position.

According to such a configuration, the container can be accurately positioned at the imaging position by the pedestal portion receiving the bottom portion of the container and the movement mechanism accurately moving the pedestal portion. Therefore, the boundary between the solid and the liquid can be detected more accurately.

(3) The solid-liquid boundary detection device may further include a holding mechanism. The holding mechanism holds the container, which is positioned at the imaging position by the movement mechanism, at the imaging position. In this case, the movement mechanism may retract the pedestal portion after the container is held at the imaging position by the holding mechanism. Further, the imaging unit may capture an image after the pedestal portion is retracted by the movement mechanism.

According to such a configuration, after the container is positioned at the imaging position by the movement mechanism, imaging can be performed after the container is held at the imaging position by the holding mechanism and the pedestal portion is retracted. As a result, in the captured image, the boundary between the solid and the liquid is not hidden by the pedestal portion, so that the boundary can be reliably detected.

(4) A pre-processing apparatus according to the invention is a pre-processing apparatus for performing pre-processing on cells, and includes a centrifugation mechanism, the solid-liquid boundary detection device, and a liquid removal mechanism. The centrifugation mechanism centrifuges a container in which a culture medium containing the cells is housed. The solid-liquid boundary detection device detects the boundary between the cells and the liquid centrifuged in the container by the centrifugation mechanism. The liquid removal mechanism removes the liquid other than the cells in the container on the basis of a position of the boundary detected by the boundary detection processor.

According to such a configuration, the boundary between the cells (solid) and the liquid which are centrifuged can be detected by the solid-liquid boundary detection device, and the liquid other than the cells in the container can be removed on the basis of the position of the boundary. Therefore, it is possible to remove almost all the liquid on the basis of the position of the boundary accurately detected by the solid-liquid boundary detection device.

(5) The liquid removal mechanism may suck and remove the liquid in the container from a tip end of a needle by inserting the needle into the container. In this case, the imaging unit may capture images before and after the needle is inserted into the liquid in the container. Further, the pre-processing apparatus may further include a needle detection processor that detects a tip end position of the needle on the basis of a difference between the images before and after the needle is inserted into the liquid in the container, which are captured by the imaging unit.

According to such a configuration, the tip end position of the needle can be easily and accurately detected on the basis of the difference between the images before and after the needle is inserted into the liquid in the container. Therefore, since the tip end of the needle can be brought as close to the boundary as possible in a range not coming into contact with the solid, on the basis of the position of the boundary accurately detected by the solid-liquid boundary detection device, almost all the liquid can be sucked by the needle and removed.

EFFECTS OF THE INVENTION

According to the invention, since the position of the boundary that becomes a shadow due to illumination does not shift due to the way the light hits, and the image is always captured at an accurate position, the boundary between the solid and the liquid can be detected more accurately.

MODE FOR CARRYING OUT THE INVENTION

1. Schematic configuration of automatic pre-processing system

Figure 1:
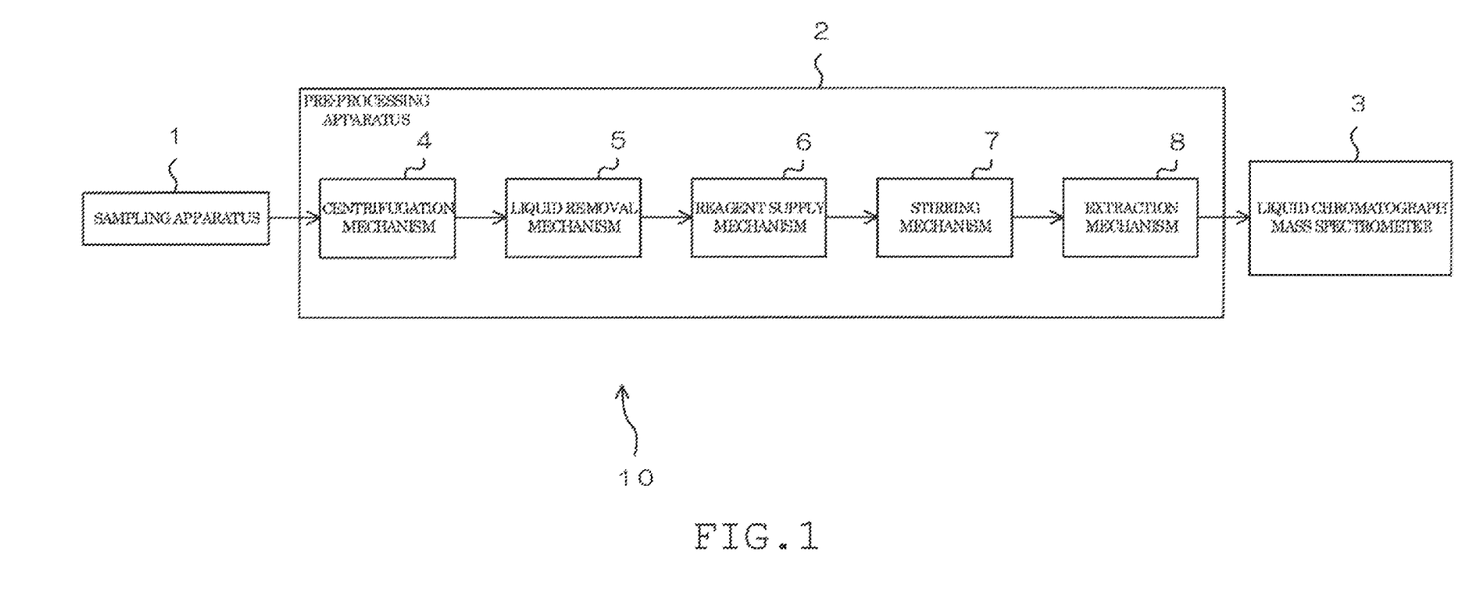
FIG. 1 is a block diagram illustrating a schematic configuration of an automatic pre-processing system including a pre-processing apparatus to which a solid-liquid boundary detection device according to an embodiment of the invention is applied.

FIG. 1 is a block diagram illustrating a schematic configuration of an automatic pre-processing system 10 including a pre-processing apparatus 2 to which a solid-liquid boundary detection device according to an embodiment of the invention is applied. The automatic pre-processing system 10 is a device for automatically performing pre-processing on an analysis target. In the present embodiment, the analysis target is, for example, a cultured cell, and more specifically, a bacterial cell.

The automatic pre-processing system 10 includes the sampling apparatus 1 and a pre-processing apparatus 2. The metabolites of the cells are extracted from the cells after the pre-processing is performed by the automatic pre-processing system 10, and are supplied to a liquid chromatograph mass spectrometer 3. The liquid chromatograph mass spectrometer 3 is only an example of an analysis device for analyzing an analysis target, and it is also possible to perform an analysis by using another analysis device.

The sampling apparatus 1 is a apparatus for sampling a liquid from a container (culture container). For example, the cells of microorganisms and plants are cultured in a culture medium in a container called a bioreactor, and the culture medium containing the cells in the bioreactor is sampled by the sampling apparatus 1. In the bioreactor, for example, a stirring member that is rotated by using magnetic force, an oxygen concentration sensor for detecting the concentration of dissolved oxygen, and the like are provided, and the cells are cultured in the sampling apparatus 1 by adjusting the dissolved oxygen concentration while stirring the culture medium in the bioreactor.

The pre-processing apparatus 2 performs pre-processing on the cells contained in the culture medium sampled from the bioreactor. In the sampling apparatus 1, the culture medium containing the cells is housed in a test tube as a container (sampling container). The pre-processing apparatus 2 is provided with a centrifugation mechanism 4, a liquid removal mechanism 5, a reagent supply mechanism 6, a stirring mechanism 7, an extraction mechanism 8, and the like, and by each of these mechanisms, the pre-processing is sequentially performed on the cells contained in the culture medium in the test tube.

The centrifugation mechanism 4 centrifuges the test tube in which the culture medium containing the cells is housed. As a result, centrifugal force is applied to the culture medium in the test tube, and the cells (solid) and the liquid other than the cells are separated. Then, the liquid other than the cells centrifuged in the test tube by the centrifugation mechanism 4 is removed by using the liquid removal mechanism 5, and thereby the cells are collected.

The reagent is supplied by the reagent supply mechanism 6, to the test tube after the liquid is removed by the liquid removal mechanism 5. As a result, the reagent is mixed with the cells in the test tube, and a mixed solution is generated. Then, the mixed solution generated by the reagent supply mechanism 6 is stirred by the stirring mechanism 7.

The reagent used in the present embodiment is a reagent for extracting metabolites in the cells, and a suspension in which the metabolites are extracted from the cells is obtained by stirring the mixed solution in which the reagent is mixed with the cells. A part of the suspension obtained in this manner is extracted as an extraction liquid by the extraction mechanism 8, and is supplied to the liquid chromatograph mass spectrometer 3.

2. Specific configuration of solid-liquid boundary detection device

Figure 2:
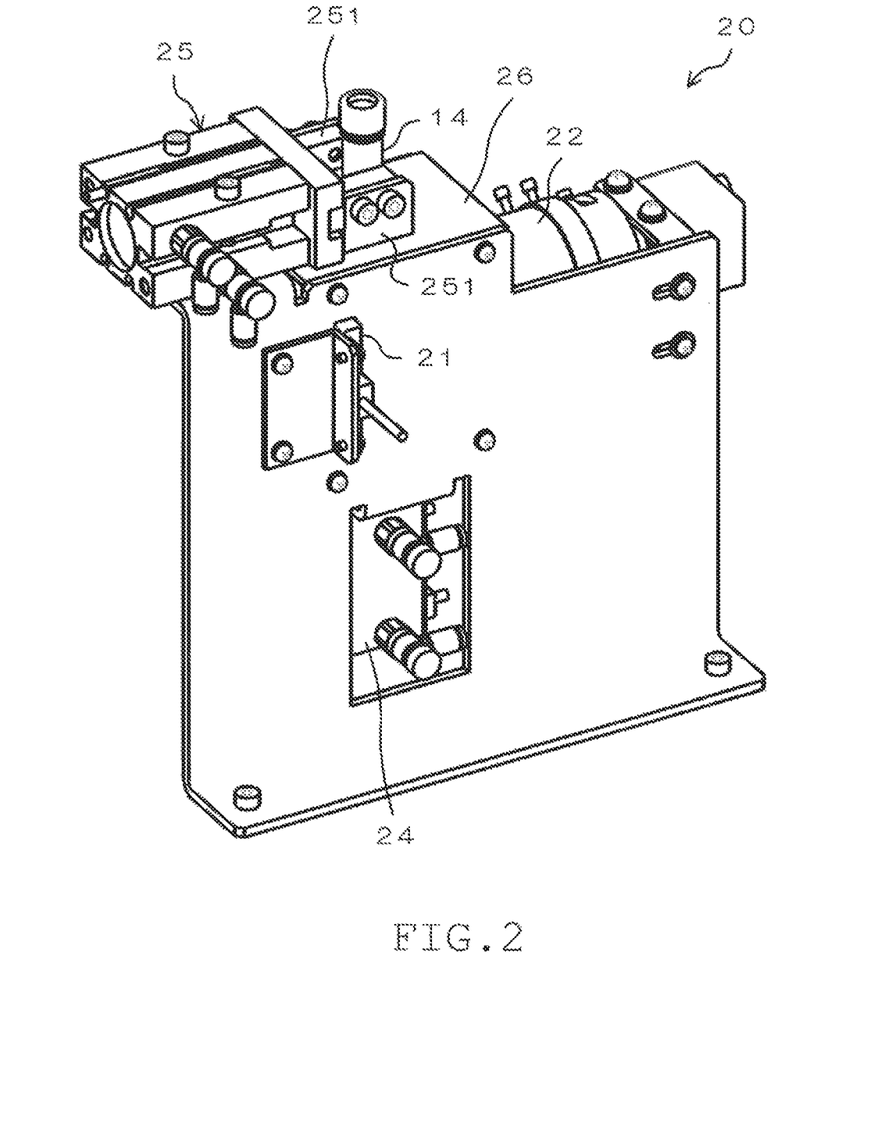
FIG. 2 is a perspective view of the solid-liquid boundary detection device.
Figure 3:
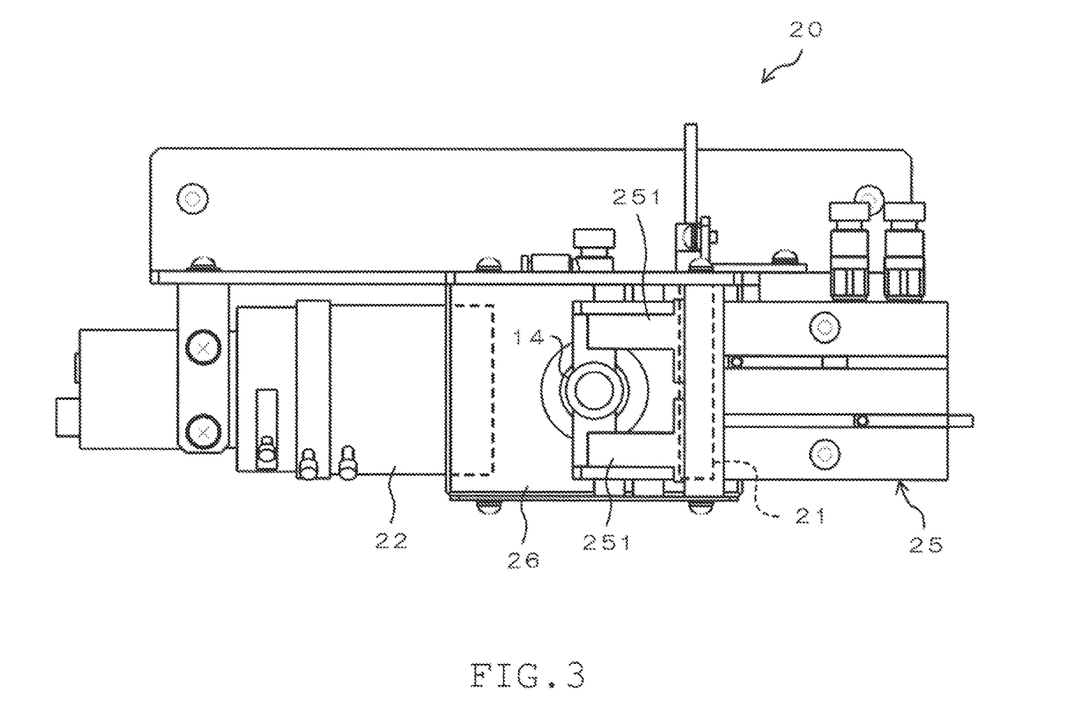
FIG. 3 is a plan view of the solid-liquid boundary detection device.
Figure 4:
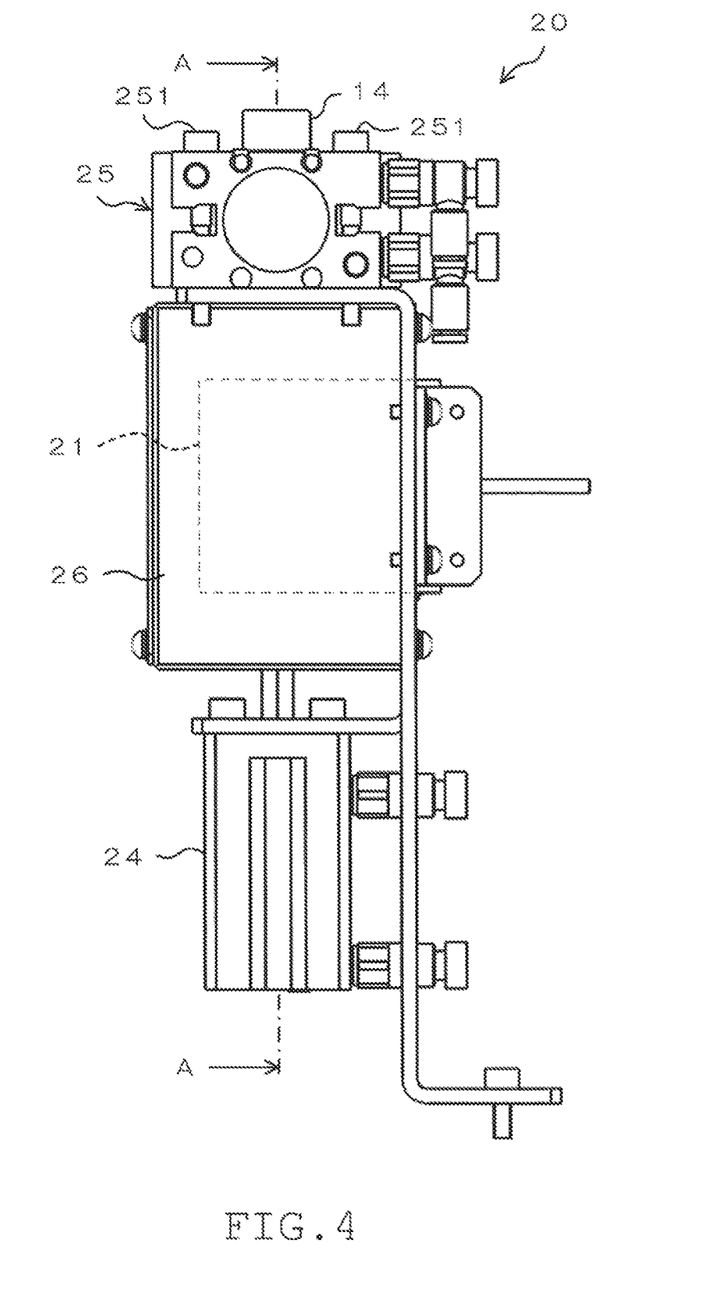
FIG. 4 is a side view of the solid-liquid boundary detection device.
Figure 5:
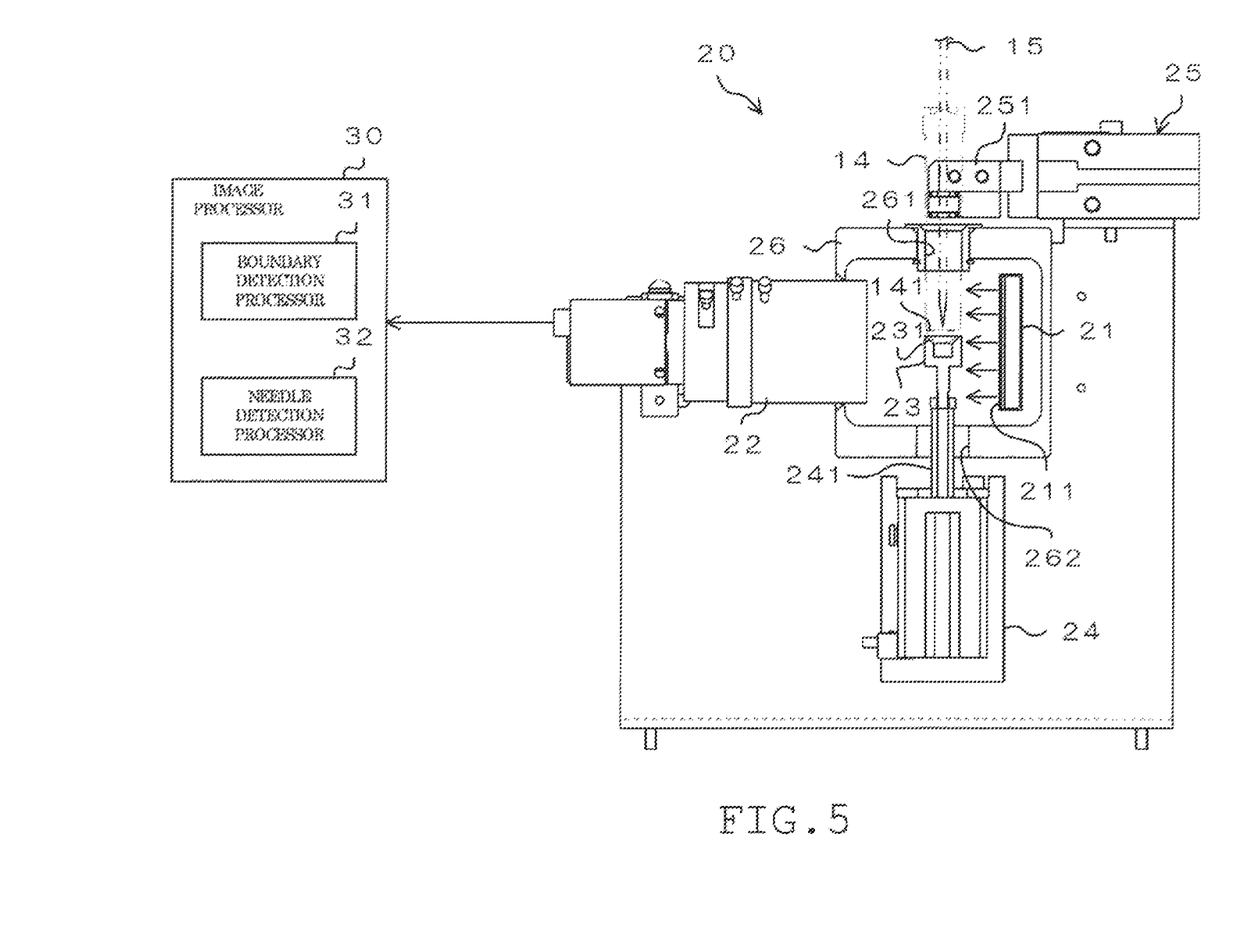
FIG. 5 is a sectional view taken along line A-A of the solid-liquid boundary detection device of FIG. 4.

FIG. 2 is a perspective view of a solid-liquid boundary detection device 20. FIG. 3 is a plan view of the solid-liquid boundary detection device 20. FIG. 4 is a side view of the solid-liquid boundary detection device 20. FIG. 5 is a sectional view taken along line A-A of the solid-liquid boundary detection device 20 of FIG. 4.

In the present embodiment, processing for detecting a boundary 141 between the solid and the liquid in a test tube 14 is performed by the solid-liquid boundary detection device 20, on the test tube 14 after the centrifugation is performed by the centrifugation mechanism 4 of the pre-processing apparatus 2 (refer to FIG. 5). That is, in the test tube 14 after the centrifugation is performed, the cells (solid) and the liquid other than the cells are separated, and the boundary 141 therebetween is detected by the solid-liquid boundary detection device 20.

After that, a needle 15 included in the liquid removal mechanism 5 is inserted into the test tube 14, and the tip end of the needle 15 is brought as close to the boundary 141 as possible in a range not coming into contact with the cells, on the basis of the position of the boundary 141 detected by the solid-liquid boundary detection device 20. By sucking the liquid from the tip end of the needle 15 in this state, almost all the liquid in the test tube 14 can be sucked and removed.

The solid-liquid boundary detection device 20 includes a surface illumination 21 that illuminates the test tube 14 from the outside, and an imaging unit 22 that is arranged on the opposite side of the test tube 14 from the surface illumination 21. The surface illumination 21 uniformly applies light from an irradiation surface 211 by surface emission. Therefore, the test tube 14 is uniformly illuminated from the outside in a vertical direction, and an image including the boundary 141 between the solid and the liquid in the illuminated test tube 14 is captured by the imaging unit 22.

In the present embodiment, since the imaging unit 22 is arranged on the opposite side of the test tube 14 from the surface illumination 21, in the image captured by the imaging unit 22, the solid part that does not transmit (or is difficult to transmit) light becomes a shadow, and the liquid part that easily transmits light becomes brighter than the solid part. Therefore, a boundary position between a shadow part and a bright part in the captured image can be detected as the position of the boundary 141.

The solid-liquid boundary detection device 20 further includes a pedestal portion 23 that receives a bottom portion of the test tube 14, a movement mechanism 24 that moves the pedestal portion 23, and a holding mechanism 25 for holding the test tube 14 at an imaging position. The imaging position is a position of the test tube 14 when imaging is performed by the imaging unit 22, and is set in advance as a position where the image including the boundary 141 can be captured by the imaging unit 22.

The pedestal portion 23 is a member in which a recess 231 is formed on an upper surface, and the convexly curved bottom portion of the test tube 14 is received in a state of being inserted into the recess 231. In the present embodiment, the test tube 14 is received by the pedestal portion 23 in a state of extending in the vertical direction. However, the test tube 14 may be configured to be received by the pedestal portion 23 in a state of extending in a direction inclined with respect to the vertical direction.

The movement mechanism 24 includes an axial portion 241 connected to the pedestal portion 23, and can move the pedestal portion 23 by sliding the axial portion 241 in an axial direction using a drive source (not illustrated) such as an air cylinder. The axial portion 241 extends in the same direction as the test tube 14 received by the pedestal portion 23. By sliding the axial portion 241, the position of the test tube 14 received by the pedestal portion 23 can be positioned at the imaging position. In this example, the axial portion 241 extends in the vertical direction, but without being limited thereto, any configuration may be adopted as long as the pedestal portion 23 can be moved in a direction intersecting the horizontal direction.

The holding mechanism 25 includes one pair of displacement portions 251. The one pair of displacement portions 251 is arranged to face each other in the horizontal direction, and the test tube 14 can be interposed between the one pair of displacement portions 251. When the test tube 14 is interposed, the one pair of displacement portions 251 is in a state of being close to each other, and the test tube 14 can be interposed therebetween. From this state, when the one pair of displacement portions 251 is separated from each other to be spaced more than the outer diameter of the test tube 14, the one pair of displacement portions 251 is in a state of not interposing the test tube 14. After the test tube 14 is positioned at the imaging position by the movement mechanism 24, when the test tube 14 is held by the holding mechanism 25 at that position, the test tube 14 can be held at the imaging position.

In the present embodiment, the periphery of the bottom portion of the test tube 14 held at the imaging position is covered with a housing 26. The housing 26 is hollow, and the bottom portion of the test tube 14 is inserted into the inside of the housing 26. An opening 261 to which the test tube 14 is inserted is formed on the upper surface of the housing 26. Further, an opening 262 to which the axial portion 241 of the movement mechanism 24 is inserted is formed on the bottom surface of the housing 26. The surface illumination 21 is arranged in the housing 26, and a part of the imaging unit 22 is inserted into the housing 26. In this way, since the periphery of the bottom portion of the test tube 14 to be imaged by the imaging unit 22 is covered with the housing 26, the influence of ambient light on the captured image can be reduced.

3. Image processing on captured image

As conceptually illustrated in FIG. 5, the solid-liquid boundary detection device 20 in the present embodiment includes an image processor 30 for performing image processing on the image captured by the imaging unit 22. The image processor 30 is composed of, for example, a personal computer, and the image processor 30 functions as a boundary detection processor 31 and a needle detection processor 32 by a central processing unit (CPU) included in the image processor 30 executing a program.

The boundary detection processor 31 performs processing of detecting the boundary 141 between the solid and the liquid in the test tube 14 from the image captured by the imaging unit 22. Specifically, the boundary position between the dark part (solid part) and the bright part (liquid part) is detected as the position of the boundary 141 on the basis of the brightness of each pixel of the captured image.

When the imaging is performed by the imaging unit 22, first, the movement mechanism 24 slides the axial portion 241 in the vertical direction to position the test tube 14 at the imaging position. Then, by the test tube 14 being held by the holding mechanism 25, after the test tube 14 is fixed at the imaging position, the movement mechanism 24 slides the axial portion 241 downward. As a result, the pedestal portion 23 is separated from the bottom portion of the test tube 14, and the pedestal portion 23 is retracted from an imaging range of the imaging unit 22.

After the pedestal portion 23 is retracted by the movement mechanism 24 in this way, the imaging is performed by the imaging unit 22. As a result, the image including the boundary 141 can be captured without the bottom portion of the test tube 14 being hidden by the pedestal portion 23. After that, the needle 15 is inserted into the test tube 14 while the test tube 14 is held at the imaging position by the holding mechanism 25.

When the needle 15 is inserted into the test tube 14, the needle 15 is lowered until the tip end of the needle 15 enters the imaging range of the imaging unit 22 and the tip end of the needle 15 reaches a position separated from the boundary 141 on the liquid side. By the imaging being performed by the imaging unit 22 in this state, the image including the boundary 141 and the tip end of the needle 15 is captured.

As described above, in the present embodiment, the image before the needle 15 is inserted into the liquid in the test tube 14 and the image after the needle 15 is inserted are captured by the imaging unit 22 without moving the position of the test tube 14. In this case, the images captured before and after the needle 15 is inserted differ only in the presence or absence of the needle 15, and the position of the boundary 141 and the like are the same.

The needle detection processor 32 detects a tip end position of the needle 15 on the basis of the difference between the images before and after the needle 15 is inserted which are captured by the imaging unit 22. That is, if the difference between the brightness of each pixel of the image before the needle 15 is inserted and the brightness of each pixel of the image after the needle 15 is inserted is calculated, a large brightness difference is calculated only in the part of the needle 15. Therefore, the tip end position of the needle 15 can be detected on the basis of the calculation result.

By detecting the position of the boundary 141 and the tip end position of the needle 15 in this way, the movement distance of the needle 15, which is required for bringing the tip end of the needle 15 as close to the boundary 141 as possible in a range not coming into contact with the solid (cell), can be calculated. After that, by lowering the needle 15 by the calculated movement distance and sucking the liquid from the tip end of the needle 15, almost all the liquid in the test tube 14 can be sucked and removed.

4. Effects (1) In the present embodiment, the test tube 14 is uniformly illuminated from the outside by the surface illumination 21, and the image of the boundary 141 between the solid (cells) and the liquid (other than the cells) in the illuminated test tube 14 can be captured by the imaging unit 22. Therefore, since the position of the boundary 141 that becomes a shadow due to illumination does not shift due to the way the light hits, and the image is always captured at an accurate position, the boundary 141 between the solid and the liquid can be detected more accurately.

(2) In the present embodiment, the test tube 14 can be accurately positioned at the imaging position by the pedestal portion 23 receiving the bottom portion of the test tube 14 and the movement mechanism 24 accurately moving the pedestal portion 23. Therefore, the boundary 141 between the solid and the liquid can be detected more accurately.

(3) In the present embodiment, after the test tube 14 is positioned at the imaging position by the movement mechanism 24, imaging can be performed after the test tube 14 is held at the imaging position by the holding mechanism 25 and the pedestal portion 23 is retracted. As a result, in the captured image, the boundary 141 between the solid and the liquid is not hidden by the pedestal portion 23, so that the boundary 141 can be reliably detected.

(4) In the present embodiment, the tip end position of the needle 15 can be easily and accurately detected on the basis of the difference between the images before and after the needle 15 is inserted into the liquid in the test tube 14. Therefore, since the tip end of the needle 15 can be brought as close to the boundary 141 as possible in a range not coming into contact with the solid, on the basis of the position of the boundary 141 accurately detected by the solid-liquid boundary detection device 20, almost all the liquid can be sucked by the needle 15 and removed.

5. Modification Example

The solid-liquid boundary detection device 20 according to the invention can be applied to any other device without being limited to the pre-processing apparatus 2. That is, the solid-liquid boundary detection device 20 can be used for detecting the boundary between the solid and the liquid in any other container without being limited to the test tube 14.

DESCRIPTION OF REFERENCE SIGNS 1 sampling apparatus
2 pre-processing apparatus
3 liquid chromatograph mass spectrometer
4 centrifugation mechanism
5 liquid removal mechanism
6 reagent supply mechanism
7 stirring mechanism
8 extraction mechanism
10 automatic pre-processing system
14 test tube
15 needle
20 solid-liquid boundary detection device
21 surface illumination
22 imaging unit
23 pedestal portion
24 movement mechanism
25 holding mechanism
26 housing
30 image processor
31 boundary detection processor
32 needle detection processor
141 boundary

The invention claimed is:

1. A solid-liquid boundary detection device configured to detect a boundary between a solid and a liquid in a container, the solid-liquid boundary detection device comprising:
a surface illumination configured to illuminate the container from outside;
an imaging unit that is arranged on an opposite side of the container from the surface illumination, and is configured to capture an image including the boundary;
a pedestal portion configured to receive a bottom portion of the container;
a movement actuator configured to move the pedestal portion in a direction intersecting a horizontal direction and position the container at an imaging position; and
a holding clasp configured to hold the container, which is positioned at the imaging position by the movement actuator, at the imaging position; and
a boundary detection processor configured to detect the boundary from the image captured by the imaging unit, wherein the movement actuator is configured to retract the pedestal portion after the container is held at the imaging position by the holding clasp, and wherein the imaging unit is configured to capture an image of the container after the pedestal portion is retracted by the movement actuator.

2. A pre-processing apparatus for performing pre-processing on cells, the pre-processing apparatus comprising:

a centrifugation mechanism that is configured to centrifuge a container in which a culture medium containing cells is housed;

a solid-liquid boundary detection device configured to detect a boundary between the cells and a liquid centrifuged in the container by the centrifugation mechanism;

a liquid removal pump that removes the liquid other than the cells in the container on the basis of a position of the boundary detected by the boundary detection processor, wherein the solid-liquid boundary detection device comprises:

a surface illumination configured to illuminate the container from outside;

an imaging unit that is arranged on an opposite side of the container from the surface illumination, and is configured to capture an image including the boundary;

a pedestal portion configured to receive a bottom portion of the container;

a movement actuator configured to move the pedestal portion in a direction intersecting a horizontal direction and position the container at an imaging position; and a holding clasp configured to hold the container, which is positioned at the imaging position by the movement actuator, at the imaging position; and a boundary detection processor configured to detect the boundary from the image captured by the imaging unit, wherein the movement actuator is configured to retract the pedestal portion after the container is held at the imaging position by the holding clasp, and wherein the imaging unit is configured to capture an image of the container after the pedestal portion is retracted by the movement actuator.

3. The pre-processing apparatus according to claim 2, wherein the liquid removal pump is configured to suck and remove the liquid in the container from a tip end of a needle by inserting the needle into the container, wherein the imaging unit is configured to capture images before and after the needle is inserted into the liquid in the container, and wherein the pre-processing apparatus further comprises a needle detection processor that is configured to detect a tip end position of the needle on the basis of a difference between the images before and after the needle is inserted into the liquid in the container, which are captured by the imaging unit.

* * * * *